(12) United States Patent
Giammanco et al.

(10) Patent No.: US 10,080,715 B1
(45) Date of Patent: Sep. 25, 2018

(54) POLYSACCHARIDE BASED MICROPARTICLES WITH IMPROVED STABILITY AND METHODS OF MAKING THE SAME

(71) Applicant: BOWLING GREEN STATE UNIVERSITY, Bowling Green, OH (US)

(72) Inventors: Giuseppe Giammanco, Mentor, OH (US); Alexis Ostrowski, Maumee, OH (US)

(73) Assignee: Bowling Green State University, Bowling Green, OH (US)

( * ) Notice: Subject to any disclaimer, the term of this patent is extended or adjusted under 35 U.S.C. 154(b) by 0 days.

(21) Appl. No.: 15/490,882

(22) Filed: Apr. 18, 2017

Related U.S. Application Data

(60) Provisional application No. 62/323,863, filed on Apr. 18, 2016.

(51) Int. Cl.
*A61K 8/73* (2006.01)
*A61K 9/00* (2006.01)
*A61K 8/19* (2006.01)
*A61K 8/02* (2006.01)
*A61Q 19/00* (2006.01)

(52) U.S. Cl.
CPC .............. *A61K 8/73* (2013.01); *A61K 8/0245* (2013.01); *A61K 8/19* (2013.01); *A61Q 19/00* (2013.01); *A61K 2800/28* (2013.01)

(58) Field of Classification Search
None
See application file for complete search history.

(56) References Cited

U.S. PATENT DOCUMENTS

2004/0033265 A1* 2/2004 Chen .................... A61K 9/1652
424/488

OTHER PUBLICATIONS

Racoviţă et al. (Revue Roumaine de Chimie, 2009, 54(9), 709-718).*
Bueno, V.B. et al., Synthesis and Swelling Behavior of Xanthan-Based Hydrogels, Carbohydrate Polymers (2013) pp. 1091-1099, vol. 92.
Eriksen, M. et al., Microplastic Pollution in the Surface Waters of the Laurentian Great Lakes, Marine Pollution Bulletin (2013) pp. 177-182, vol. 77.
Rochman, C.M. et al., Scientific Evidence Supports a Ban on Microbeads., Environmental Science & Technology (2015) pp. 10759-10761, vol. 49.
Microbead-Free Waters Act of 2015 (H.R. 1321).
Grand View Research, Inc. Organic Personal Care Market Worth $15.98 Billion by 2020 Grand View Research, Inc. (Aug. 27, 2015), PRNewswire.
Frendall, L.S. and Sewell, M.A. Contributing to Marine Pollution by Washing Your Face: Microplastics in Facial Cleansers, Marine Pollution Bulletin (2009) pp. 1223-1228, vol. 58.
Wu, Sarah, Why the President Banned Your Go-To Face Wash (and Why That's a Really Good Thing), Teen Vogue (Jan. 8, 2016), found at https://www.teenvogue.com/story/microbead-ban-in-beauty-products.

* cited by examiner

*Primary Examiner* — Bong-Sook Baek
(74) *Attorney, Agent, or Firm* — Marshall & Melhorn, LLC

(57) ABSTRACT

The invention relates to a process for preparing polysaccharide-based microparticles with improved mechanical properties and hydrolytic stability. The spherical particles are useful as exfoliating agents in cosmetic formulations, in replacement of the newly banned plastic microbeads. The method comprises the preparation of hydrogel particles, drying of the particles, and a solid-state reaction that results in the covalent stabilization of the material. The invention also encompasses microparticles made using the method.

12 Claims, 4 Drawing Sheets

|  | Synthetic bead (PE) | MICRO PARTICLES | Raw material (Pumice) |
|---|---|---|---|
| Biodegradability | ✗ | ✓ | ✓ |
| Biocompatibility | ✓ | ✓ | ✓ |
| Performance | ✓ | ✓ | ✗ |
| Processability | ✓ | ✓ | ✗ |

POLYSACCHARIDE BASED MICROPARTICLES WITH IMPROVED STABILITY AND METHODS OF MAKING THE SAME

FIELD OF THE INVENTION

The present invention relates to a process for preparing polysaccharide-based microparticles with improved mechanical properties and hydrolytic stability. The present invention also relates to the microparticles made by the processes described herein.

BACKGROUND OF THE INVENTION

Plastic microbeads (PMs) were recently placed in the spotlight after the discovery of tons of these tiny pieces of petrochemical polymers being accumulated in lakes, rivers and oceans. Scientific studies reported that 808 trillion microbeads are being washed down household drains every day in the US. Although these bits of polymer are used in a variety of applications, cosmetic products are by far the first source of PMs in the waste water streams. These microparticles are used as the abrasive ingredient in some toothpaste and as exfoliating agent in many shower gels, facial scrubs. The popularity of these particles lays in their low costs of production on one hand, and their good performance and stability on the other.

Typical plastic microbeads are smaller than 5 mm in diameter and are usually made form polyethylene (PE), polypropylene (PP), polymethylmethacrylate (PMMA), and in some cases, polyesters and polyamides. Unfortunately, the small size of PMs makes it hard for any water treatment plant to extract them from the water streams. Moreover, the high stability of these inert particles turns them into a big environmental problem, as they are spreading over the water bodies around the world and they have no hurry to degrade and disappear. To make the problem even worse, the plastic in these beads has high affinity for many toxic chemicals present in wastewaters. These chemicals are absorbed and adsorbed by the microparticles, which serve as vehicles to these poisonous chemicals that end up dispersed in the ocean. One of the most recent alarming findings is the presence of these poison-loaded microparticles in many animal species around the world.

A joined effort of different organizations and lawmakers gave birth to the Microbead-Free Waters act of 2015, an initiative that was turned into a national law on December of that year, when President Obama signed the bill. The new legislation mandates to phase out the manufacture of personal care products containing PMs by July 2017, and the sale of such cosmetic products by 2018, in the 50 states of the country. Other countries such as Canada, Australia, Germany and the UK are creating consciousness and following this example.

These changes in the statutory framework are compelling any company that sells PMs containing products to look for viable alternatives to the outlawed scrubbing particles. The webpage bitthemicrobread.org reports a list of 63 personal care product manufacturers that have publicly pledged to replace PMs in their products on or before 2017.

The transition, however, is not going to be easy, as it requires doing changes in the formulation, supplier chains, cost structure, etc. In fact, some companies represented by the Personal Care Products Council (PCPC), are trying to find loopholes in the new legislature, by tweaking the definition of "plastic microbeads". This would allow these companies to replace the traditional PE or PP beads by other pernicious polylmeric materials. As it looks, some of the alternatives that these "rebellious" companies are considering are compostable plastic (CPs) such as cellulose acetate (the same present in cigarette butts) or polydroxyalcanoates (used in compostable cups and food containers). Although CPs can be degraded by microorganisms, high temperatures, acidic or alkaline conditions, or a combination of them; these materials are not better than the petrochemical microbeads, as they would not biodegrade in the marine environmental and they will still be strange bodies floating in our waters for, at least, tens of years.

As more people are becoming conscious of the impact that our everyday activities have on the environment and ecosystems, they are changing their habits in a positive way; users are becoming educated about the products they are buying, and the demand for environmentally friendly products is increasing. The cosmetic industry is a good example of this; the organic cosmetics' market is expected to grow at a compound annual growth rate of 9.6% from 2014 to 2020, when the global market is expected to reach $15.98 Billion. The industry for greener cosmetics blooms, as people are willing to pay more for products they can relate to as safer or healthier.

Although some brands have been offering natural alternatives to PMs for a while now, there does not seem to be an overtaking of the market by these solutions. Ground nutshells, pumice and natural waxes are among the frequently found raw exfoliating materials, but rice, coffee and almond grounds can be also found in some facial scrubs. The main limitation of these raw materials is that the functionality of the particles is restricted to the size of the grain, and there is little room for modification and optimization. For example, a facial scrub where the exfoliating agent is too harsh (pumice is a good example of this) is recommended for use at a lower frequency that the equivalent product formulated with PMs.

Limitations like this one represent an inconvenient both for the end user who does not want to use a potentially hurtful product, and the cosmetic manufacturer, who will try to avoid a drop in the sales of the product. The legal panorama leaves only two options to the cosmetic industry: to use the one of these natural, but off-putting, alternatives, or innovate and design new materials to revolutionize the field.

A different kind of solution is compulsory: an alternative as bio-friendly as the currently available raw scrubbing materials, but with the ability to adjust its properties according to the needs of the final product. The reader will agree that best alternative should, at the very least, feel and look as the traditional PMs do. To achieve this, it is essential to have a processable material that can be formulated, shaped and sized as desired with high reproducibility. The new alternative also needs to be 100% environmentally friendly to comply with the new legal framework.

The best solution to this problem needs to come from nature itself, yet in a way where the quality and properties of the final product can be controlled. Ideally, the solution will be to use macromolecules from plant origin as building blocks to create the new microparticles. By using 100% natural and FDA approved materials, biocompatibility of the microparticles is ensured.

Alginate-based hydrogel particles and beads have being around for years and different patents and publications present them as devices for cell encapsulation, drug delivery, cosmetic applications, food technology, etc. These hydrogels comprising alginate and other anionic polysaccharides are formed by electrostatic interactions between the biomolecule and an oppositely charged element (ionotropic gelation), usually a multivalent metal, in most cases is calcium. The resulting material is mechanically stable, has high affinity for water, is biocompatible, and biodegradable.

There is, however, a big limitation of these materials; and it is related to the hydrolytic stability of the gels. The nature of the interaction between the components of the gel makes it susceptible to degradation if the pH, ionic strength, temperature, or chemical composition of the environment change beyond certain levels. The outcome is a change in the gel volume, mechanical properties, and often dissolution of the material. This instability makes it difficult to use these gels for cosmetic applications, where complex mixtures of different chemicals are present, and the stability and shelf life of the final product is very important. One of the most common ingredients in soaps and shampoos, for instance, is EDTA. EDTA is used to chelate metal ions and improve the stability of the formulations. If a calcium-alginate hydrogel is added to a product containing this substance, the outcome would be the sequestration of the calcium by the EDTA and the complete disintegration of the hydrogel particle.

Different strategies for improving the hydrolytic stability of these polysaccharide gels include using mixtures of polysaccharides during the preparation of the gels, binding the particle in a layer to layer approach, or using other charged polymers for creating coatings on the surface of the hydrogel bead. None of these approaches yields a stable material that can endure the action of EDTA without undergoing degradation.

The method described herein combines the preparation of hydrogel particles, drying of the particles, and a solid-state reaction that results in the stabilization of the material and results in a microparticle with the following attributes:
- Natural ingredients: Natural plant extracts are used to formulate materials.
- Bio-friendly process: Process is 100% petrochemicals free and water is the only solvent used
- Stability: Hydrolytic stability was tested in hand soap and in 2% EDTA solution. Beads are stable after 1 month, 40° C.
- Color: Particles present a clear color that can be modified if desired.
- Odor: Unlike some natural alternatives (coffee grounds, almonds, coconut, etc.) particles are odor free
- Degradability: Being made from natural, plant-derived materials, the microparticles made in accordance with the embodiments of the invention are susceptible to enzymatic and hydrolytic degradation.
- Size: Process allows for controlling the size of the particles with access to the micron and millimeter scales
- Textures: Unlike some raw materials, microparticles produced in accordance with the embodiments of the invention do not present sharp edges that may cause laceration of the skin.

SUMMARY OF THE INVENTION

The present invention is directed toward a method of making polysaccharide based microparticles by dissolving a first polysaccharide in water; thereby creating a first mixture; adding a second polysaccharide to the first mixture, thereby creating a second mixture; mixing citric acid into the second mixture, thereby creating a polysaccharide solution; and placing drops of the polysaccharide solution into a metal ion solution, thereby forming microparticles. The method may further use the steps of removing the microparticles from the metal ion solution; rinsing the microparticles with deionized water; rinsing the microparticles with ethanol; and drying the microparticles.

A polysaccharide based microparticle made using the method is also disclosed. In other embodiments, a polysaccharide based microparticle with a first polysaccharide; a second polysaccharide cross-linked to the first polysaccharide; and a metal cation is disclosed.

BRIEF DESCRIPTION OF THE DRAWINGS

The above, as well as other advantages of the present invention, will become readily apparent to those skilled in the art from the following detailed description when considered in the light of the accompanying drawings in which.

DETAILED DESCRIPTION

In one embodiment the invention, a first mixture is prepared by dissolving a gel-forming polysaccharide (it should be specifically one that contains a carboxylic acid group, so all polyuronic acids (for example, but not limited to: alginate, pectin, pectate, oxidized starch, or combinations thereof) in water, preferably at room temperature, to get a final 1-6% w/v solution of the polysaccharide(s). In other embodiments, a final 1.2-5% w/v solution of the polysaccharide is achieved. In still other embodiments, a final 1.4-4% w/v solution of the polysaccharide is achieved. In still other embodiments, a final 1.5-3% w/v solution of the polysaccharide is achieved.

Next, a second polysaccharide is added to the first mixture to get a final concentration of 0.1-1% w/v and thereby forming a second mixture. The second polysaccharide can be any polysaccharide. The second polysaccharide is used to tune the mechanical properties and swelling properties of the microparticle. In one embodiment, the second polysaccharide is xanthan gum.

Finally, some citric acid is dissolved in the second mixture to get a final concentration in the range of 0.1-1% w/v and thereby form a polysaccharide solution. As for the citric acid, without being bound by theory, one could assume that it remains inside the bead during the formation of the metal-first polysaccharide complex (described below). In some embodiments, this complex will be a citrate-alginate metal complex. In some embodiments, the ratio of citrate to the first polysaccharide is the same in the final gel microparticle as it was in the polysaccharide mixture. That being said, again, without being bound by theory, in the final step of the process, where the microparticles are dried, involves a solid state reaction in which the citrate reacts, most probably through a condensation reaction and cross links the polysaccharides, forming the insoluble microparticle.

Figure 1:
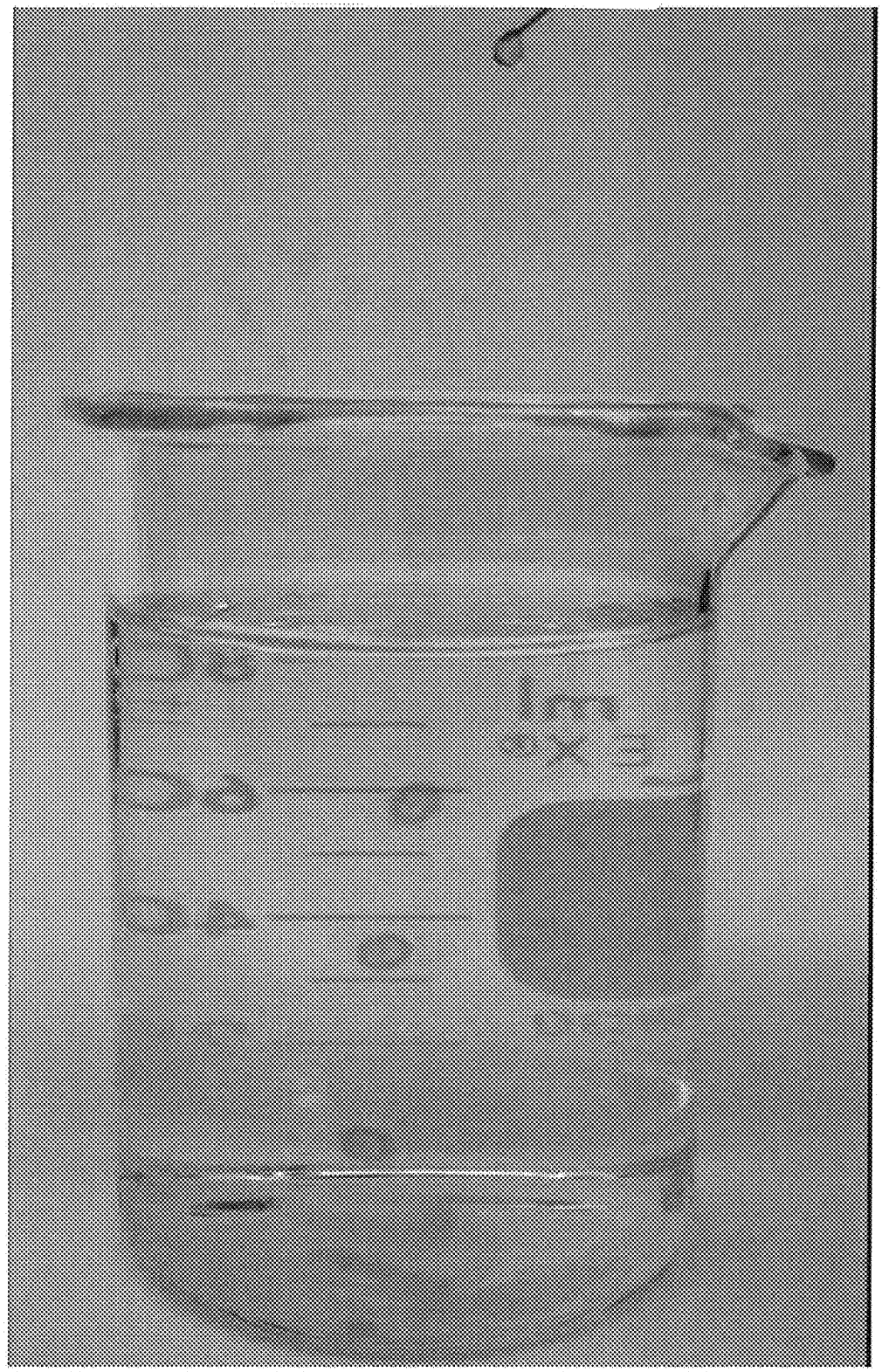
FIG. 1 is a still from a video (at 6 seconds) showing the formation of the microbeads in one embodiment of the invention.
Figure 2:
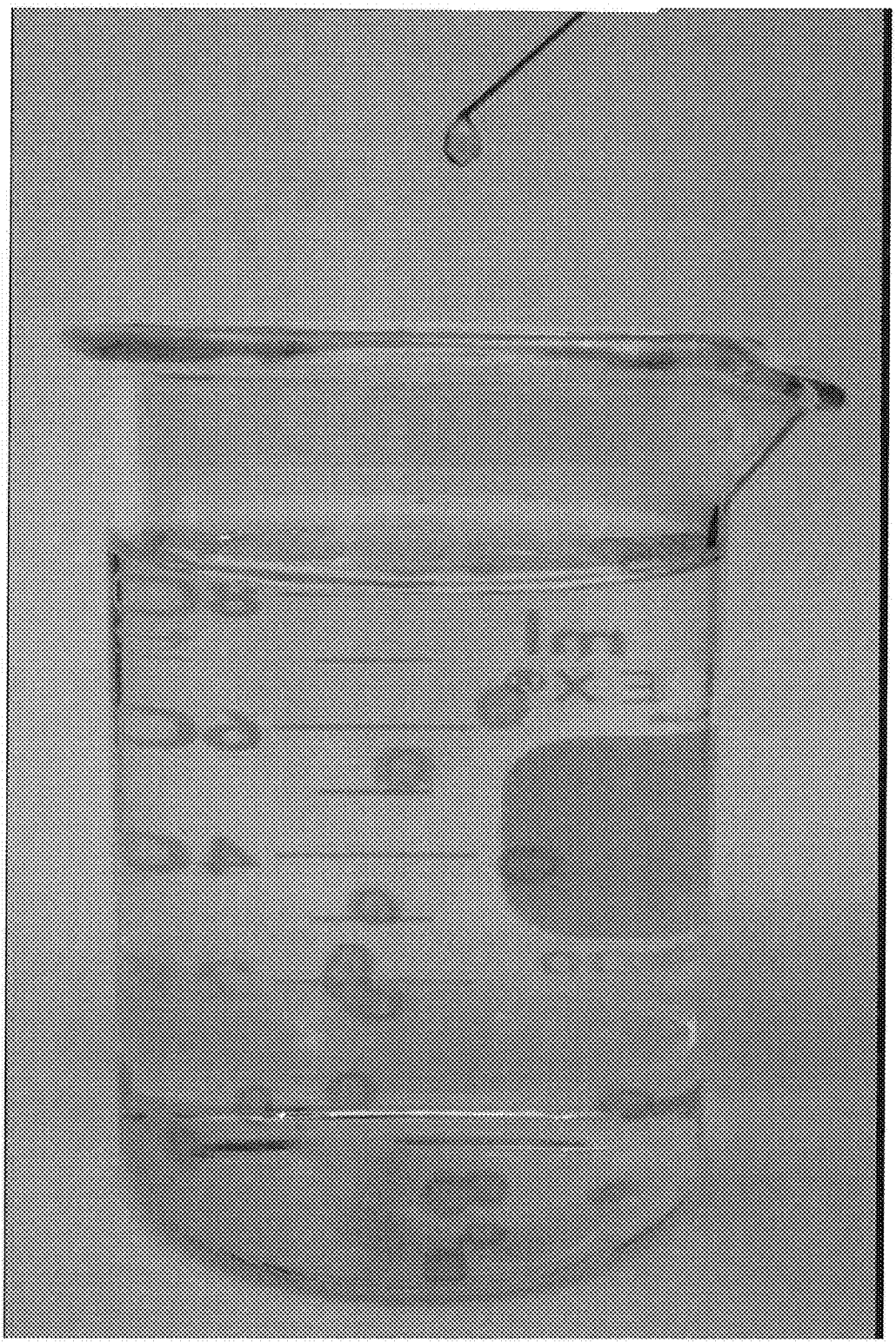
FIG. 2 is a still from a video (at 15 seconds) showing the formation of the microbeads in one embodiment of the invention.
Figure 3:
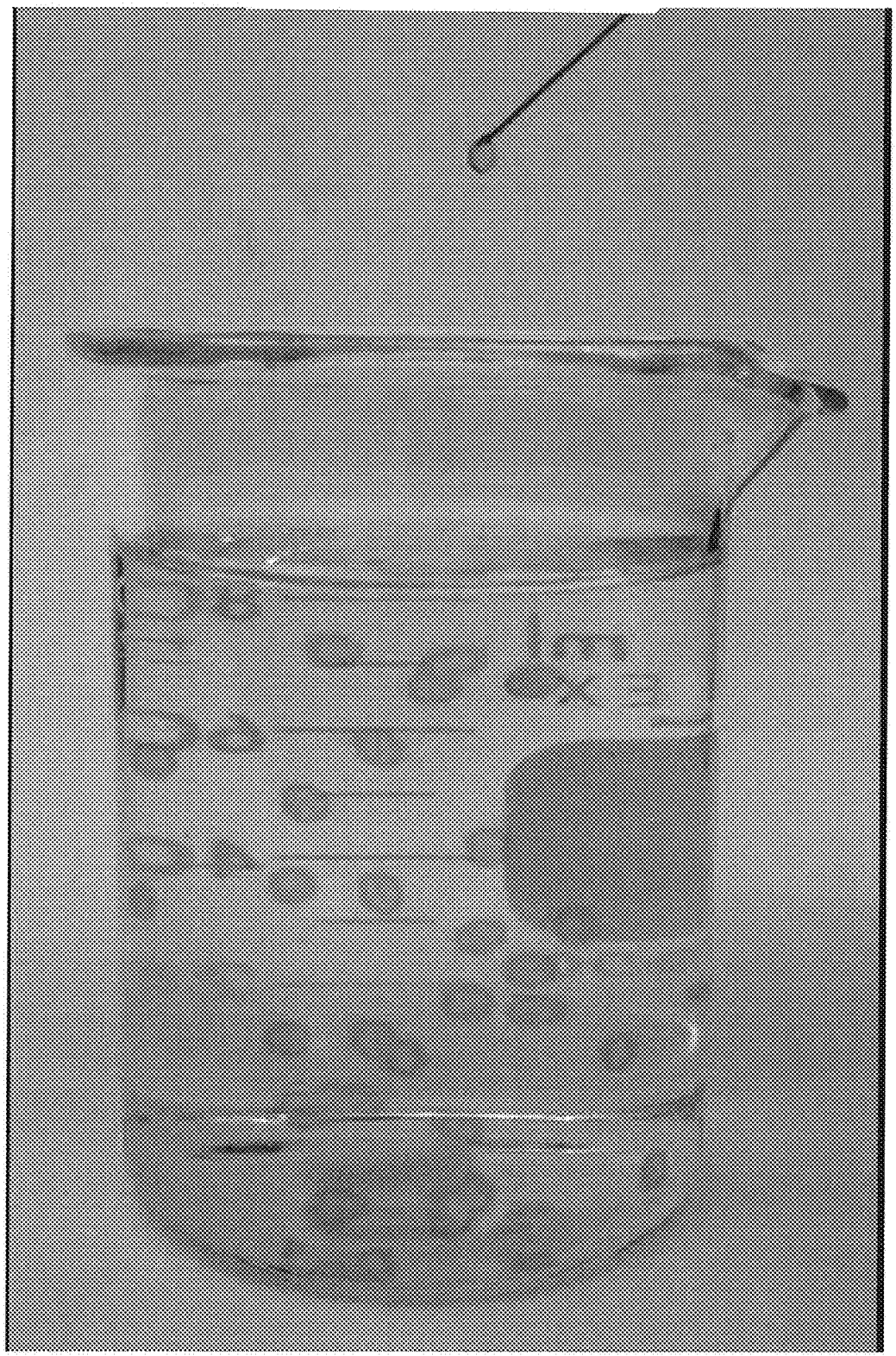
FIG. 3 is a still from a video (at 23 seconds) showing the formation of the microbeads in one embodiment of the invention.

In the next step, drops of the polysaccharide solution are nebulized or simply dripped into a metal ion solution. FIGS. 1-3 show progressive stills (at 6 s, 15 s and 23 s, respectively) from a video showing the process. In some embodiments, the metal ion solution is a 0.05-0.5 M solution. In some embodiments, the metal ion could be $Ca^{++}$, $Mg^{++}$, $Ba^{++}$ or $Zn^{++}$. In alternative embodiments, other divalent metal ions such as, but not limited to, $Fe++$ or $Cu^{++}$, or trivalent metal ions ($Fe^{+++}$, $Al^{+++}$, $Eu^{+++}$, $Ga^{+++}$, $La^{+++}$, $Va^{+++}$, $Cr^{+++}$, or $Ti^{+++}$) may be used. The anion can be chloride, bromide, nitrate, sulphate, lactate, gluconate, or any other, as far as the salt is soluble in whatever medium is used (in preferred embodiments, the medium will be water).

The function of the metal cations is to form a coordination complex with the first polysaccharide. The formation of this complex is what turns each liquid drop into a gel bead. The gel bead serves as the scaffold for producing the final solid micro particle. The metal is therefore an important part of the structure of the system.

The microparticles form immediately after the polysaccharide solution and metal ion solution get in contact. The microparticles are left sitting in the metal ion solution for 1 min-1 h. After removal, they are rinsed first with deionized water and then with ethanol with a small amount (0.1-5% w/v) of an alcohol (methanol, ethanol or isopropyl alcohol). The alcohol is needed so the microparticles don't stick to each other as they dry.

In some embodiments, the drying process was usually performed for 12 h at the selected temperature (20-50° C.) at atmospheric pressure. The drying process can be anywhere from 6-16 hours and can vary depending on temperature and pressure used. In various embodiments, the microparticles shrink by 20-50%, 30-40%, 32-38%, or 35%.

The final step can be performed by heating the material in an oven at atmospheric pressure or under vacuum (−15 in Hg) at 130-160° C. for 2-4 h causes solid-state reactions to take place that result in the covalent crosslinking of the material (Carbohydrate Polymers 92 (2013) 1091-1099). The resulting particles present improved hydrolytic stability in water and EDTA solutions.

Different combinations of polysaccharides/temperature/time afford particles with different properties, ranging from those which will not swell at all, to those undergoing different degrees of swelling. Hydrolytic stability can be defined as the invariability of the texture and swelling volume of these materials when immersed in aqueous solutions for long periods of time.

In addition, by changing the time and temperature of the solid state reaction, one can modulate the cross lining density and, therefore, the stability and swellability of the final microparticle.

Figure 4:
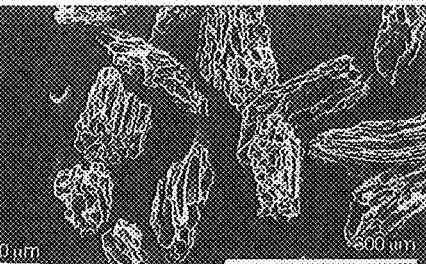
FIG. 4 shows a micrograph comparing a microparticle of one embodiment of the invention to plastic beads and pumice.

FIG. 4 shows a micrograph comparing a microparticle of one embodiment of the invention to plastic beads and pumice.

Figure 5:
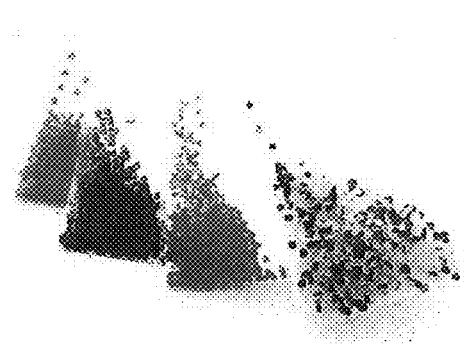
FIG. 5 shows microparticles created in accordance with an embodiment of the invention with different color dyes added.

FIG. 5 shows microparticles created in accordance with an embodiment of the invention with different color dyes added.

In accordance with the provisions of the patent statutes, the present invention has been described in what is considered to represent its preferred embodiments. However, it should be noted that the invention can be practiced otherwise than as specifically illustrated and described without departing from its spirit or scope.

What is claimed is:

1. A method of making polysaccharide based microparticles, the method comprising the steps of:
   a. dissolving a first polysaccharide in water; thereby creating a first mixture;
   b. adding a second polysaccharide to the first mixture, thereby creating a second mixture;
   c. mixing citric acid into the second mixture, thereby creating a polysaccharide solution; and
   d. placing drops of the polysaccharide solution into a metal ion solution, thereby forming microparticles wherein the first polysaccharide contains a carboxylic acid group and the second polysaccharide is xanthan gum.

2. The method of claim 1 further comprising the steps of:
   e. removing the microparticles from the metal ion solution;
   f. rinsing the microparticles with deionized water;
   g. rinsing the microparticles with ethanol; and
   h. drying the microparticles.

3. The method of claim 1 wherein the first polysaccharide is a polyuronic acid.

4. The method of claim 1 wherein the said first polysaccharide is selected from the group consisting of: alginate, pectin, pectate, oxidized starch, and a combination thereof.

5. The method of claim 1 wherein the first mixture has a percentage of said first polysaccharide selected from the group consisting of: 1-6%, 1.2-5%, 1.4-4%, and 1.5-3%.

6. The method of claim 1 wherein the second mixture has a percentage of said second polysaccharide of 0.1-1%.

7. The method of claim 1 wherein the polysaccharide solution has a percentage of citric acid of 0.1-1%.

8. The method of claim 1 wherein the metal ion solution is 0.05-0.5M.

9. The method of claim 2 wherein the drying of the microparticles occurs at a temperature selected from the group consisting of: 20-50° C. and 130-160° C.

10. The method of claim 2 wherein the drying of the microparticles is performed at atmospheric pressure.

11. The method of claim 2 wherein the drying of the microparticles is performed at −15 in Hg.

12. A polysaccharide based microparticle made using the method of claim 1.

* * * * *